US006975904B1

(12) United States Patent
Sloman

(10) Patent No.: US 6,975,904 B1
(45) Date of Patent: Dec. 13, 2005

(54) MODIFICATION OF EVOKED RESPONSE DETECTION ALGORITHM BASED ON ORIENTATION AND ACTIVITY OF PATIENT

(75) Inventor: Laurence S. Sloman, Los Angeles, CA (US)

(73) Assignee: Pacesetter, Inc., Sylmar, CA (US)

( * ) Notice: Subject to any disclaimer, the term of this patent is extended or adjusted under 35 U.S.C. 154(b) by 621 days.

(21) Appl. No.: 10/053,462

(22) Filed: Nov. 8, 2001

(51) Int. Cl.$^7$ ................................................. A61N 1/37
(52) U.S. Cl. ....................................... 607/28; 600/510
(58) Field of Search ................................ 600/508, 510, 600/513, 515–518; 607/4, 9, 11, 17–28

(56) References Cited

U.S. PATENT DOCUMENTS

| | | | |
|---|---|---|---|
| 4,686,988 A | 8/1987 | Sholder | 128/419 PT |
| 4,708,142 A | 11/1987 | DeCote, Jr. | 128/419 PT |
| 4,712,555 A | 12/1987 | Thornander et al. | 128/419 PTG |
| 4,729,376 A | 3/1988 | DeCote, Jr. | 128/419 PT |
| 4,788,980 A | 12/1988 | Mann et al. | 128/419 PG |
| 4,940,052 A | 7/1990 | Mann et al. | 128/419 PG |
| 4,944,298 A | 7/1990 | Sholder | 128/419 PG |
| 4,969,467 A | 11/1990 | Callaghan et al. | 128/419 PG |
| 5,184,615 A * | 2/1993 | Nappholz et al. | 607/14 |
| 5,466,254 A | 11/1995 | Helland | 607/123 |
| 5,472,453 A * | 12/1995 | Alt | 607/4 |
| 5,476,483 A | 12/1995 | Bornzin et al. | 607/17 |
| 5,573,550 A | 11/1996 | Zadeh et al. | 607/28 |
| 5,683,427 A * | 11/1997 | Ekwall | 607/11 |
| 5,685,315 A | 11/1997 | McClure et al. | 128/708 |
| 6,192,275 B1 * | 2/2001 | Zhu et al. | 607/28 |
| 6,445,949 B1 * | 9/2002 | Kroll | 607/4 |
| 6,738,666 B1 * | 5/2004 | Park et al. | 607/18 |

\* cited by examiner

*Primary Examiner*—Robert E. Pezzuto
*Assistant Examiner*—Kristen Mullen

(57) ABSTRACT

Optimization of evoked response detection in an automatic capture detection system employed by an implantable cardiac stimulation device is presented. Patient state information is used to determine the appropriate settings of variables that are associated with the evoked response signal detection algorithm. The variables used by the evoked response signal detection algorithm are first established for the patient in a variety of positions. During operation of the implantable cardiac stimulation device, the patient state is monitored and the variables used by the evoked response signal detection algorithm are adjusted accordingly.

19 Claims, 5 Drawing Sheets

MODIFICATION OF EVOKED RESPONSE DETECTION ALGORITHM BASED ON ORIENTATION AND ACTIVITY OF PATIENT

FIELD OF INVENTION

This invention relates generally to implantable cardiac stimulation devices and, more particularly, to systems and methods for determining an amount of electrical stimulation required to induce a cardiac contraction in a patient.

BACKGROUND

A pacemaker is an implantable device that delivers electrical stimulation pulses to cardiac tissue to relieve symptoms associated with bradycardia—a condition in which a patient cannot maintain a physiologically acceptable heart rate. Early pacemakers delivered stimulation pulses at regular intervals in order to maintain a predetermined heart rate, which was typically set at a rate deemed to be appropriate for the patient at rest. The predetermined rate was usually set at the time the pacemaker was implanted, although in more advanced devices, the rate could be set remotely by a medical practitioner after implantation.

Early advances in pacemaker technology included the ability to sense intrinsic cardiac activity, i.e., the intracardiac electrogram, or "IEGM" signal. This led to the development of "demand pacemakers," so named because they deliver stimulation pulses only as needed by the heart. Demand pacemakers are capable of detecting a spontaneous cardiac contraction that occurs within a predetermined time period (commonly referred to as the "escape interval") following a preceding contraction, whether spontaneous or evoked by the implantable device. When a naturally occurring contraction is detected within the escape interval, a demand pacemaker does not deliver a pacing pulse.

Pacemakers such as those described above proved to be extremely beneficial in that they successfully reduced or eliminated seriously debilitating and potentially lethal effects of bradycardia in many patients. However, since pacemakers are implantable devices, an invasive surgical procedure is required, and many patients who receive pacemakers must undergo several surgical procedures, because pacemakers have a limited life span, due to limited battery life, and require periodic replacement. Of course, it is desirable to minimize the number of surgical procedures that must be performed on a patient to improve safety and reduce costs.

The life span of most pacemakers is dictated by the rate at which their batteries drain. Thus, a substantial effort has been directed toward minimizing the amount of energy used by pacemakers, while ensuring that the devices continue to deliver effective therapy. Demand pacemakers effectively reduce battery drain by delivering pacing pulses only when required. However, each pacing pulse delivered by a demand pacemaker may have a significantly higher energy content than that required for inducing a cardiac contraction. Thus, even after the development of demand pacemakers, there remained an opportunity for further improvements in the area of pacemaker energy utilization.

The minimum amount of electrical stimulation that effectively evokes a cardiac contraction is commonly referred to as a patient's "capture threshold." Unfortunately, capture threshold varies significantly among patients; therefore, the amount of electrical stimulation provided by a pacemaker cannot be permanently set by the manufacturer. Rather, stimulus parameters must be individually set for each patient immediately after implantation and during subsequent office visits.

Determining a particular patient's capture threshold is a relatively simple procedure when performed during an office visit. Essentially, the medical practitioner can remotely adjust the amount of electrical stimulation downward from a maximum value that is known to elicit a contraction for all patients. Once the amount of electrical stimulation falls below the patient's capture threshold, an ensuing heartbeat is not detected, and the medical practitioner upwardly adjusts the amount of electrical stimulation beyond the last successful level.

Typically, a substantial safety margin is added to the measured capture threshold to ensure that the pacemaker continues to evoke contractions over an extended period of time. The safety margin is necessary because a patient's capture threshold varies over time—sometimes dramatically during the first few months following implantation. However, by adding such a large safety margin, it is almost assured that the pacemaker will be wasting significant amounts of energy during its life span.

In an effort to reduce the amount of energy wasted, pacemakers have been developed that automatically evaluate the patient's capture threshold during normal operation. These devices are also capable of automatically adjusting the amount of electrical stimulation in response to changes to the capture threshold. These features, which in combination are referred to herein as "automatic capture detection", significantly reduce unnecessary battery drain, because higher energy pacing pulses are delivered only when needed by the patient. Although most of these devices continue to add a safety margin to the measured capture threshold, the safety margin can be greatly reduced, especially when the capture threshold is measured frequently.

Pacemakers that perform automatic capture detection commonly monitor a patient's IEGM signal to determine what pulsing energy level is necessary to evoke a responsive cardiac contraction ("evoked response"). In particular, the pacemaker samples the portion of the patient's IEGM signal corresponding to the evoked response, if any, immediately after a pacing pulse is delivered. The shape of the waveform indicates whether the pacing pulse successfully captured the heart (i.e., whether the pulse caused a corresponding contraction of the heart chamber).

However, known automatic capture detection methods have several drawbacks, particularly relating to signal processing, which have proven difficult to overcome. For example, it is extremely difficult to accurately sense the evoked response immediately after a pacing pulse is delivered, due to the presence of residual electrical effects in the immediate vicinity of the pacing electrodes. These residual effects (commonly known as "polarization") interfere with the pacemaker's ability to detect an evoked response. Indeed, most pacemakers enter a refractory period immediately after a pacing pulse is delivered, during which time the sensing circuitry is deactivated, for the specific purpose of avoiding undesirable sensing of polarization.

An additional drawback of conventional pacemakers that perform automatic capture detection is detection of an evoked response signal that may vary in its morphology. This variability can be introduced by many physiological factors, including the patient's drug therapy and circadian rhythm. One particular factor that contributes to a large variation in the morphology of the evoked response is the patient's posture and/or level of activity. For example, differences in the morphology of an evoked response signal from a single patient have been observed when the patient is standing, sitting, lying down, at rest, or active (e.g., exercising or other form of moderate or strenuous activity), hereinafter referred to as the "patient state." Conventional automatic capture detection systems and methods do not consider patient state-induced variability when detecting the evoked response, or when setting the evoked response detection threshold or any other device parameters that are susceptible to such variability.

SUMMARY OF THE INVENTION

The present invention is directed to systems and methods for monitoring patient state information and, based upon such patient state information, altering certain device parameters, such as those in automatic evoked response detection algorithms, used in cardiac stimulation devices such as pacemakers.

In one embodiment, patient state information that is provided by 1) a position or posture sensor, 2) an activity or other suitable physiologic sensor, or 3) any combination thereof, is used to adjust device parameters, such as one or more parameters in an evoked response ("ER") detection algorithm within an automatic capture detection-enabled implantable cardiac stimulation device. The ER detection algorithm is modified to account for predictable changes in the morphology of the ER signal relating to the present patient state (i.e., posture and activity level). For example, the ER detection algorithm may be modified to account for slight changes in the slope, amplitude, or width of the ER signal associated with a particular patient state.

In another embodiment, certain predetermined detection thresholds are established using a standard ER sensitivity test. The standard test may be conducted with the patient in a variety of states, for example, standing, lying, at rest, and active. Once the ER sensitivity test has been conducted, the variables associated with the ER detection algorithm can be appropriately set for the respective patient states in order to calibrate the device. This process may be repeated for numerous alternative patient states. During automatic capture ER detection, the detection thresholds are preferably continuously updated based upon current patient state information.

In yet another embodiment, the capture threshold may automatically change with a change in patient state. For example, the device may automatically adjust itself to a new set of parameter values (e.g., amplitude, pulse width, and the like) to adjust for a change in patient state. In a still further embodiment, other device parameters may be adjusted automatically with changes in patient state.

In one embodiment an activity or other physiologic sensor is used to detect an activity level of the patient, such as, e.g., asleep or at rest ("low activity" state), or mild to strenuous exertion ("high activity" state). An activity sensor may also be used to infer whether the patient is in a lying or sitting (supine) position, or in a standing (upright) position. The activity level is then correlated to a patient state.

In another embodiment, a posture or position sensor is used to detect an activity level of the patient, e.g., by associating a "low activity" state with being in a lying or sitting (supine) posture, and a "high activity" state as being in a standing (upright) posture, or in the process of changing from one posture to another. The activity level is then correlated to a patient state. In still further embodiments, both activity and posture sensors are employed.

In one aspect of the invention, an automatic capture detection function may be temporarily disabled in order to prevent an inaccurate loss of capture detection while a patient is in the process of changing position, or when the sensed activity level exceeds some threshold value. For example, the ER signal morphology may be undetectable during a shift in position by a patient or when the patient is too active, i.e., where the ER is changing a significant amount. The automatic capture detection function may be temporarily disabled to account for an undetectable ER signal, thus preventing an erroneous loss of capture detection by the automatic capture detection system. In one embodiment of the invention, the output energy of the implantable cardiac stimulating device is increased during this period to ensure capture.

Other aspects and features of the invention will become apparent from consideration of the following detailed description, taken in conjunction with the accompanying drawings.

BRIEF DESCRIPTION OF THE DRAWINGS

Preferred embodiments are illustrated by way of example and not by way of limitation, in the figures of the accompanying drawings, in which like reference numerals refer to like components, and in which.

DETAILED DESCRIPTION OF PREFERRED EMBODIMENTS

Figure 1:
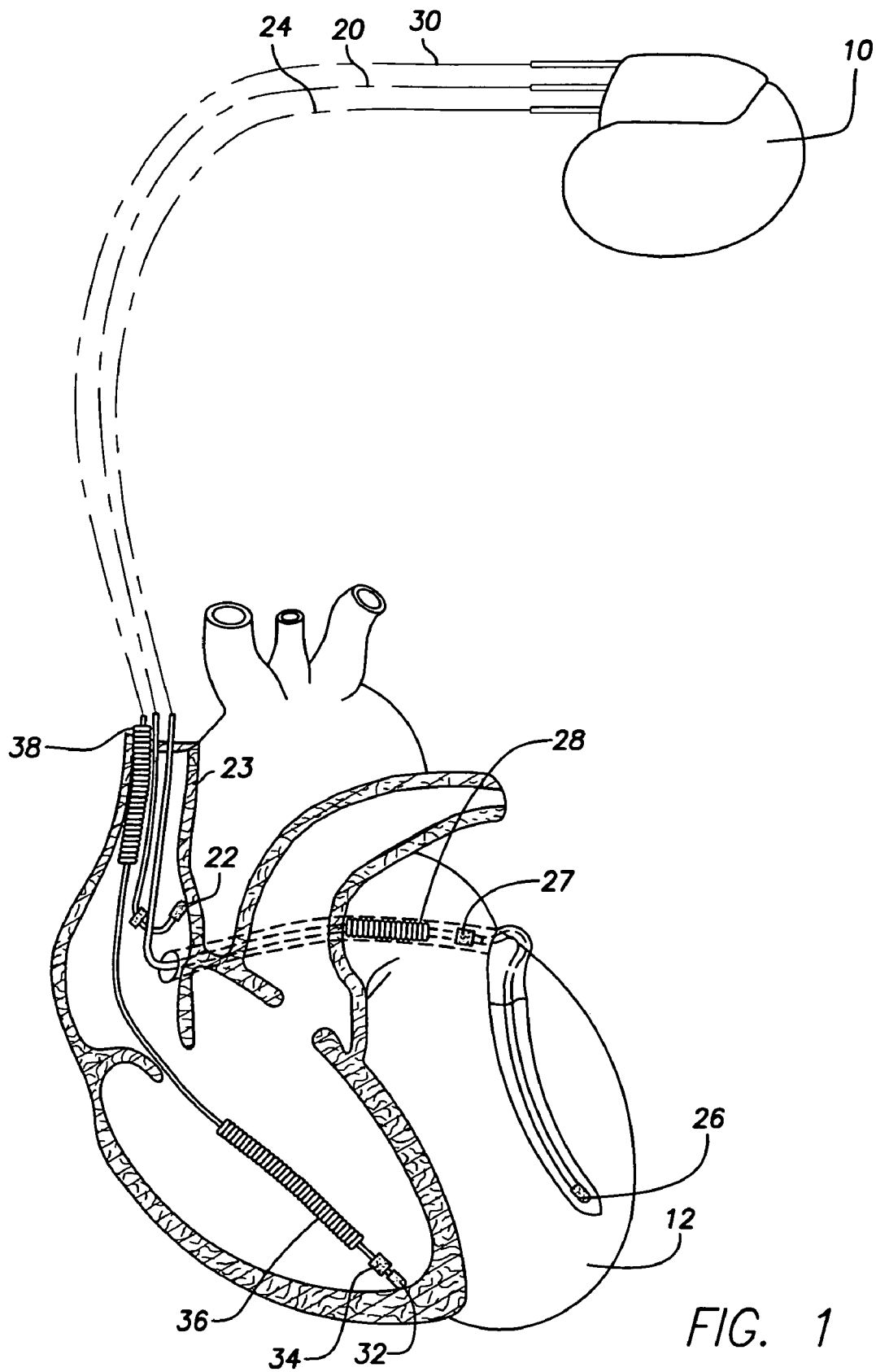
FIG. 1 is a simplified diagram illustrating an implantable stimulation device in electrical communication with plural leads implanted into a patient's heart for delivering multi-chamber stimulation and shock therapy.

FIG. 1 is a diagram illustrating an implantable stimulation device in electrical communication with three leads implanted into a patient's heart for delivering multi-chamber stimulation and shock therapy according to one embodiment of the invention. The present invention may be used with as few as one lead and may be used for pacing in any chamber of the heart. The number of leads used, and the location(s) of attachment to the heart, will depend on the particular patient's condition as is well known in the relevant art(s). For example, in one dual-chamber pacing embodiment, the implantable stimulation device includes two leads that are adapted to be positioned within the right atrium and the right ventricle of the heart, respectively, so as to enable delivery of pacing pulses and sensing of heart activity in both the right atrium and right ventricle. The present invention is suitable for use with various implantable stimulation devices, including pacemakers and combined pacemaker/ defibrillator/cardioverter devices. Thus, as used herein, the term "implantable stimulation device" refers to various different types of devices.

As shown in FIG. 1, in one embodiment a stimulation device 10 is in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having an atrial tip electrode 22, which typically is implanted in the patient's right atrial appendage. Moreover, the implantable right atrial lead 20 includes an atrial ring electrode 23 located relatively near the atrial tip electrode 22. This proximity enables localized bipolar sensing of an evoked response within the right atrium of the heart 12, thereby reducing sensing of extraneous myopotentials, as is well understood in the art. In addition, this proximity enables sensing of an evoked response with the atrial ring electrode 23. Preferably, at least one electrode used in the sensing vector is located relatively close to the electrode used to deliver the stimulation pulse, or the same electrode may be used for both stimulating and sensing.

Each electrode used for both delivery of stimulation pulses and sensing of evoked responses is preferably designed to reduce polarization on the electrode. Such polarization-reducing designs include increased surface geometry and specialized electrode coatings, as is well known in the art.

To sense left atrial and ventricular cardiac signals and to provide left chamber pacing therapy, the stimulation device 10 is coupled to a "coronary sinus" lead 24 designed for placement in the "coronary sinus region" via the coronary sinus os for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using a left ventricular tip electrode 26, left atrial pacing therapy using a left atrial ring electrode 27, and shocking therapy using a left atrial coil electrode 28. For a complete description of a coronary sinus lead, see U.S. patent application Ser. No. 09/457,277, filed Dec. 8, 1999, entitled "A Self-Anchoring, Steerable Coronary Sinus Lead" (Pianca et al.); and U.S. Pat. No. 5,466,254, "Coronary Sinus Lead with Atrial Sensing Capability" (Helland), which patents are hereby incorporated herein by reference.

The stimulation device 10 is also shown in electrical communication with the patient's heart 12 by way of an implantable right ventricular lead 30 having, in one illustrative embodiment, a right ventricular tip electrode 32, a right ventricular ring electrode 34, a right ventricular (RV) coil electrode 36, and an SVC coil electrode 38. The right ventricular ring electrode 34 is located relatively near the right ventricular tip electrode 32. This proximity enables localized bipolar sensing of an evoked response within the right ventricle of the heart 12, thereby reducing sensing of extraneous myopotentials, as is well understood in the art. In addition, this proximity enables sensing of an evoked response with the right ventricular ring electrode 34. Preferably, at least one electrode used in the sensing vector is located relatively close to the electrode used to deliver the stimulation pulse, or the same electrode may be used for both stimulating and sensing.

Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
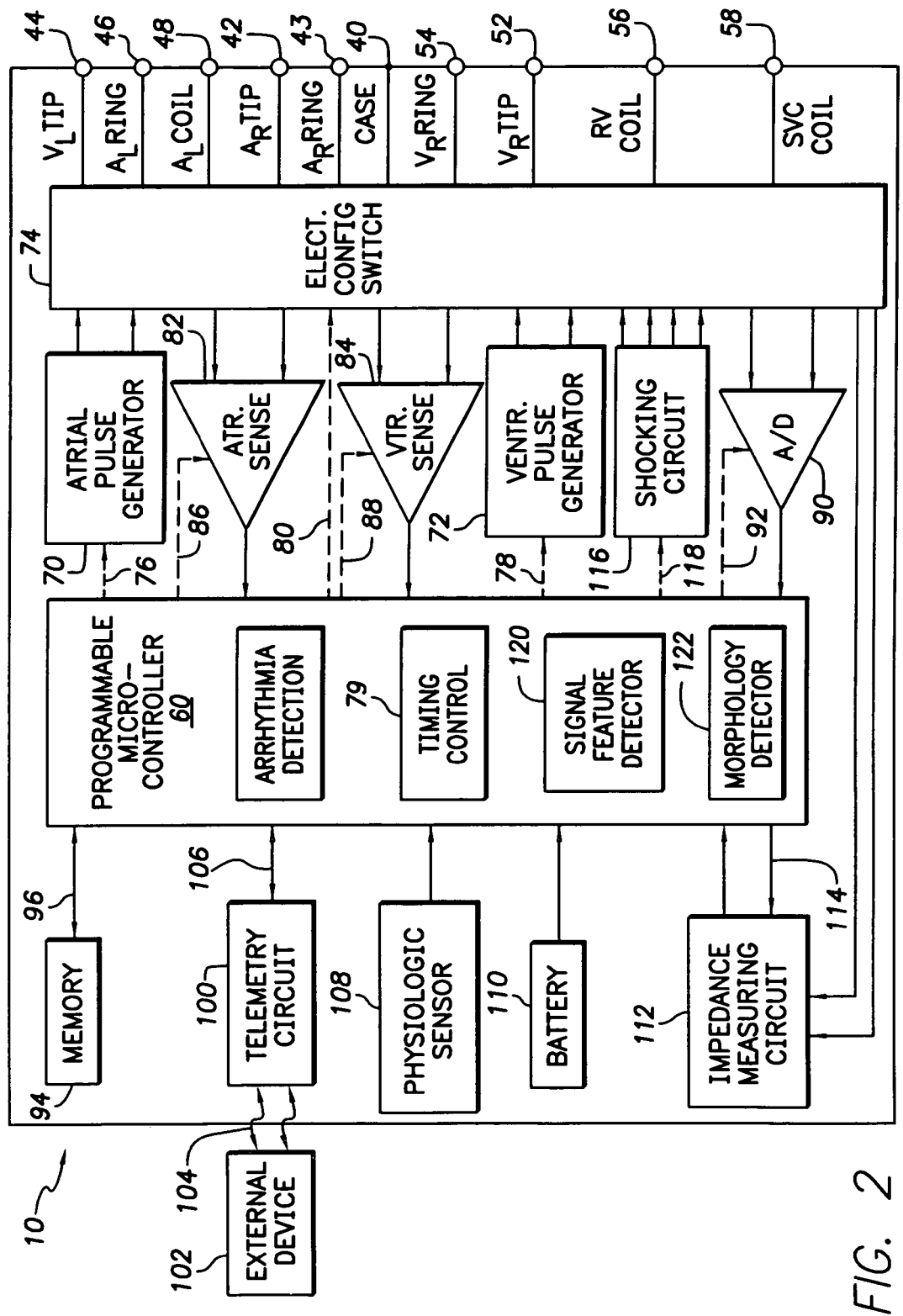
FIG. 2 is a functional block diagram of a multi-chamber implantable stimulation device illustrating the basic elements of a stimulation device that provides cardioversion, defibrillation and pacing stimulation in multiple chambers of the heart.

FIG. 2 is a functional block diagram of a multi-chamber implantable stimulation device illustrating the basic elements of a stimulation device which can provide cardioversion, defibrillation and pacing stimulation in four chambers of the heart according to one embodiment. As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 43, 44, 46, 48, 52, 54, 56, and 58 (shown schematically and, for convenience, the names of the electrodes to which they are connected are shown next to the terminals). As such, to achieve right atrial sensing and pacing, the connector includes a right atrial tip terminal (AR TIP) 42 adapted for connection to the atrial tip electrode 22 and a right atrial ring terminal ($A_R$ RING) 43 adapted for connection to the atrial ring electrode 23.

To achieve left chamber sensing, pacing and shocking, the connector includes a left ventricular tip terminal ($V_L$ TIP) 44, a left atrial ring terminal ($A_L$ RING) 46, and a left atrial shocking terminal ($A_L$ COIL) 48, which are adapted for connection to the left ventricular tip electrode 26, the left atrial ring electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

Representative types of control circuitry that may be used with the invention include the microprocessor-based control system of U.S. Pat. No. 4,940,052, entitled "Microprocessor Controlled Rate-Responsive Pacemaker Having Automatic Rate Response Threshold Adjustment" (Mann et al.); the state-machine of U.S. Pat. No. 4,712,555, entitled "Physiologically Responsive Pacemaker and Method of Adjusting the Pacing Interval Thereof" (Thornander et al.); and U.S. Pat. No. 4,944,298, entitled "Atrial Rate Based Programmable Pacemaker with Automatic Mode Switching Means" (Sholder). For a more detailed description of the various timing intervals used within the stimulation device and their inter-relationship, see U.S. Pat. No. 4,788,980, entitled "Pacemaker Having PVC Response and PMT Terminating Features" (Mann et al.). The '052, '555, '298 and '980 patents are hereby incorporated herein by reference.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity. Moreover, the switch 74 preferably includes a small resistor for electrically connecting a lead electrode, which has been used to deliver a stimulation pulse, with the case 40, thereby enabling rapid reduction of polarization on the stimulation electrode prior to using that same electrode for sensing evoked response.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing low amplitude signal characteristics of atrial or ventricular fibrillation.

For a complete description of a typical sensing circuit, see U.S. Pat. No. 5,573,550, entitled "Implantable Stimulation Device Having a Low Noise, Low Power, Precision Amplifier for Amplifying Cardiac Signals" (Zadeh et al.). For a complete description of an automatic gain control system, see U.S. Pat. No. 5,685,315, entitled "Cardiac Arrhythmia Detection System for an Implantable Stimulation Device" (McClure et al.). Accordingly, the '550 and the '315 patents are hereby incorporated herein by reference.

The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry (not shown), and the timing of any blocking circuitry (not shown) coupled to the inputs of the sensing circuits, 82 and 86, as is known in the art.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-=tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Preferably, the data acquisition system 90 is coupled with the microcontroller 60, and/or other detection circuitry, for detecting an evoked response and/or a lead polarization signal from the heart 12 in response to an applied stimulus, thereby aiding in the detection of "capture" and "loss-of-capture" (LOC). In an alternative embodiment, the data acquisition system 90 is built into the microcontroller 60, whereby digital signals representative of cardiac activity are generated by a control program designed to sample atrial and/or ventricular cardiac signals acquired by the atrial and ventricular sensing circuits, 82 and 84.

Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on a detection feature, such as the amplitude, determines if capture has occurred.

Capture detection may occur on a beat-by-beat basis or on a sampled basis. Preferably, a capture threshold search is performed once a day during the acute phase (e.g., the first 30 days) and less frequently thereafter. A capture threshold search would begin at a desired starting point (either a high energy level or the level at which capture is currently occurring) and decrease the energy level until capture is lost. The value at which capture is lost is known as the capture threshold. Thereafter, a safety margin is added to the capture threshold.

The implementation of capture detection circuitry and algorithms are well known. See for example, U.S. Pat. No. 4,729,376, entitled "Cardiac Pacer and Method Providing Means for Periodically Determining Capture Threshold and Adjusting Pulse Output Level Accordingly" (Decote, Jr.); U.S. Pat. No. 4,708,142, entitled "Automatic Cardiac Capture Threshold Determination System and Method" (Decote, Jr.); U.S. Pat. No. 4,686,988, entitled "Pacemaker System and Method for Measuring and Monitoring Cardiac Activity and for Determining and Maintaining Capture" (Sholder); and U.S. Pat. No. 4,969,467, entitled "Pacemaker with Improved Automatic Output Regulation" (Callaghan et al.). These patents are hereby incorporated herein by reference.

The microcontroller 60 is further coupled to a memory 94 by a suitable data/address bus 96. The microcontroller 60 uses the memory 94 for storage of control data used in controlling the operation of the stimulation device 10. The control data comprises programmable operating parameters, which can be stored and modified, as needed, to customize the operation of the stimulation device 10 for a particular patient. Such operating parameters define, for example, pacing pulse amplitude, pulse duration, electrode polarity, rate, sensitivity, signal sampling, automatic features, arrhythmia detection criteria, and the amplitude, waveshape and vector of each shocking pulse to be delivered to the patient's heart 12 within each respective tier of therapy.

The microcontroller 60 also uses the memory 94 for periodic recording of historical data acquired by the data acquisition system 90. This historical data comprises both patient data and device data. Thus a treating physician may use this historical data to review the performance of the implanted stimulation device 10 and the function of the heart 12 during follow-up visits. This historical data may also be used for subsequent analysis to guide the programming of the stimulation device 10, either by a human programmer or by the stimulation device 10 itself.

Advantageously, the historical data may be non-invasively downloaded from memory 94 and the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104. Examples of this established communication link 104 include an electromagnetic telemetry link and a remote communication link such as a pair of modems interconnected via a telecommunications link and equipped with telemetry capabilities.

In alternative embodiments, the stimulation device 10 includes one or more physiologic sensors 108, such as activity sensors, minute ventilation sensors, and the like. These physiologic sensors 108 are commonly referred to as "rate-responsive" sensors because they are typically used to adjust pacing stimulation rate according to the exercise state of the patient. However, the physiological sensors 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses. As is described in more detail below, in one embodiment the signals from sensor(s) 108 are used to select appropriate parameters for an evoked response detection algorithm.

In addition, one or more of the physiologic sensors 108 may be posture or position sensors that are designed to discriminate between various positions of the patient's body. For example, the posture or position sensors may discriminate between an upright or vertical position and a prone or supine position. As is described in more detail below, such signals are then used by microcontroller 60 to select appropriate parameters for an evoked response detection algorithm. Thus, as used herein, "physiologic sensor" refers to sensors that detect activity, cardiac output, and the like, as well as sensors that can detect a patient's position or posture.

While shown as being included within the stimulation device 10, it is to be understood that the physiologic sensor(s) 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter which corresponds to the exercise state of the patient. In addition, those sensors that detect the patient's position or posture may also be used, either alone or in combination with other sensors, as is described in more detail below.

In a preferred embodiment, the stimulation device 10 utilizes a "sleep state" or diurnal detection routine that can discriminate between sleep and wake states in the patient. One such discriminator is referred to as "activity variance," wherein an activity sensor is monitored diurnally to detect the low variance in the measurement corresponding to the sleep state. For a complete description of the activity variance measurement, see U.S. Pat. No. 5,476,483 (Bornzin et. al), which is hereby incorporated by reference for all that it discloses.

The stimulation device additionally includes a battery 110 that provides operating power to all of the circuits shown in FIG. 2. In an embodiment of the stimulation device 10 that employs shocking therapy, the battery 110 is preferably capable of operating at low current drains for long periods of time, and of providing high-current pulses (for capacitor charging) when the patient requires a shock pulse. In this embodiment, the battery 110 also preferably has a predictable discharge characteristic so that elective replacement time can be detected. Accordingly, in one embodiment, the device 10 preferably employs lithium/silver vanadium oxide batteries, as is true for most (if not all) current devices.

In one embodiment, the stimulation device 10 further includes magnet detection circuitry (not shown), coupled to the microcontroller 60. It is the purpose of the magnet detection circuitry to detect when a magnet is placed over the stimulation device 10, which magnet may be used by a clinician to perform various test functions of the stimulation device 10 and/or to signal the microcontroller 60 that the external programmer 102 is in place to receive or transmit data to the microcontroller 60 through the telemetry circuits 100.

In another alternative embodiment, the device 10 includes an impedance measuring circuit 112 that is enabled by the microcontroller 60 via a control signal 114. The known uses for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used. The impedance measuring circuit 112 is not critical to the present invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40 Joules), as controlled by the microcontroller 60. Such shocking pulses are preferably applied to the patient's heart 12 through two shocking electrodes, and as shown in this embodiment, selected from the left atrial coil electrode 28, the RV coil electrode 36, and/or the SVC coil electrode 38. As noted above, the housing 40 may act as an active electrode in combination with the RV coil electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

The operation of the stimulation device 10 is generally controlled by a control program stored in the memory 94 and executed by the microcontroller 60. In one embodiment, this control program comprises multiple integrated program modules, with each module bearing responsibility for controlling one or more functions of the stimulation device 10. For example, one program module may control the delivery of stimulating pulses to the heart 12, while another may control the verification of ventricular capture and the determination of ventricular pacing energy output. As shown, the capture verification module may include a signal feature detector module 120 and a morphology detector module 122. In effect, each program module is a control program dedicated to a specific function or set of functions of the stimulation device 10.

Figure 3:
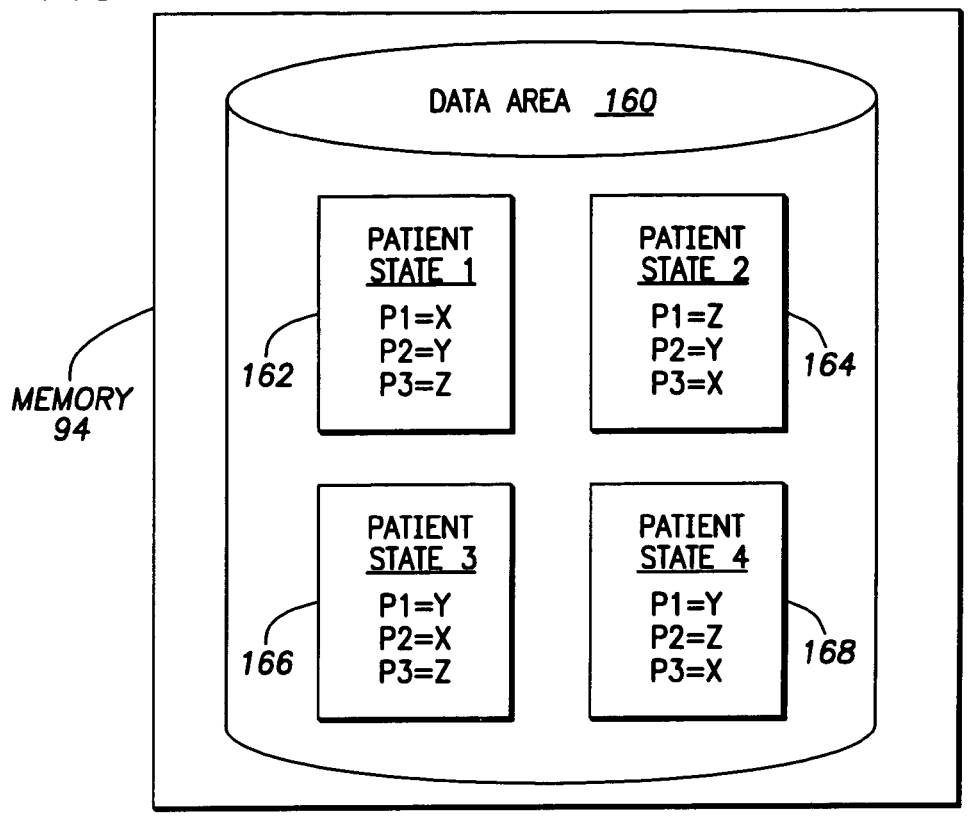
FIG. 3 is a block diagram of an exemplary memory structure for use in a stimulation device, such as the device of FIG. 2.

In accordance with a general aspect of the invention, memory 94 includes programmable control parameters corresponding to various features and functional algorithms that can be modified, as needed, to customize operation of the stimulation device 10 for a particular patient. In one preferred embodiment, the programmable parameters include one or more sets of ER detection values corresponding to each of one or more patient states. For example, memory 94 may include one or more sets of values 162, 164, 166, and 168 (FIG. 3) corresponding to the respective patient states.

Each set of values 162–168 may advantageously represent evoked response signal data expected for a particular patient state. A plurality of states may be represented, as indicated by Position 1 in set 162, Position 2 in set 164, Position 3 in set 166 and Position n in set 168. Furthermore, each set of values may contain a plurality of parameters, for example P1, P2, and P3, corresponding the pacing pulse amplitude, pulse duration, electrode polarity, rate, sensitivity, signal sampling, automatic features, arrhythmia detection criteria, patient position or posture, patient activity level, and the amplitude, slope, and width of an expected evoked response signal for the particular patient state. As described above, representative examples of various patient states include, by way of example, lying down, standing, and exercising states.

Figure 4:
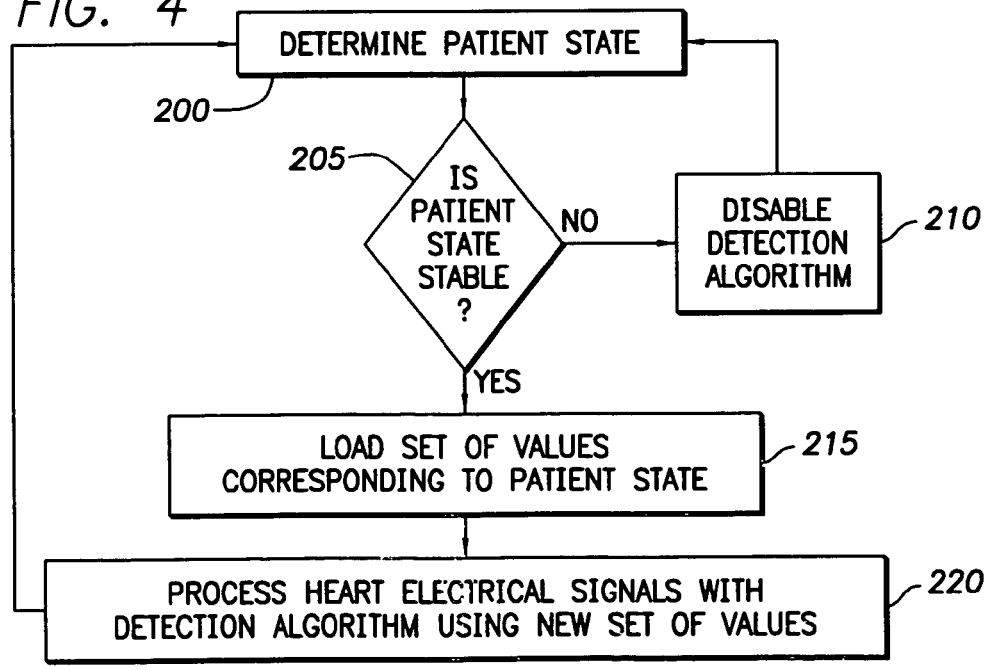
FIG. 4 is a flowchart describing an overview of an operation of one embodiment of the present invention.

In FIG. 4, a flow chart is shown describing an overview of the operation and novel features implemented in one embodiment of the device 10. In this flow chart, and the other flow charts described herein, the various algorithmic steps are summarized in individual "blocks". Such blocks describe specific actions or decisions that are carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

Initially, in step 200, the patient state (e.g., based on posture or activity or both) of the patient is determined. The posture may be determined from a position or posture sensor device that generates a signal indicative of the current posture or position of the patient. Additionally, the posture may be determined from the signals generated by an activity sensor device, which are then processed to determine the current orientation of the patient, for example by determining the activity variance for the patient, as is described above. In one embodiment, based on the output of both the position and activity sensors, various patient states can be determined, as is shown in the table below. Additional devices or methods of determining the current orientation of the patient may also be employed, as are well understood in the art.

TABLE 1

Patient States

| Activity Sensor Output | Posture Sensor Output | Patient State |
| --- | --- | --- |
| Very Low | Supine | Sleep |
| Low | Supine | Resting/Lying Down |
| Low | Upright | Standing |
| High | Upright | Exercising/Active |

Once the posture of the patient has been determined, in step 205 a determination is made as to whether the patient state is stable or indicates excessive activity, such as during exercise. Such a determination may be made by processing signals from the activity sensor to determine whether they exceed some preset threshold value, as is well known in the art. In addition, sudden or continuous changes in the signals from the position sensor may also indicate that the patient is active or at least not in a stable patient state. If the patient is determined to be active or not in a stable patient state, then the evoked response detection and the automatic capture detection functions may be disabled, temporarily, in order to avoid a false loss of capture determination, as illustrated in step 210. A loss of capture determination results when the pacing pulse delivered by the stimulation device fails to cause the heart to contract. Upon a loss of capture determination, the automatic capture detection process may immediately deliver a high-output pulse to the heart to ensure capture. A false loss of capture determination may result in an unnecessary stimulus being delivered to the patient, both wasting battery power and endangering the patient. Advantageously, the loss of capture process is avoided when the evoked response may be undetectable due to patient activity. Once the automatic capture detection function has been temporarily disabled, the process may begin anew upon receipt of additional patient orientation data.

When device 10 determines that the patient is not active and that the patient state is stable, an appropriate set of values is loaded into the control program from memory 94, as shown in step 215. The set of values is selected based upon the determined patient state, and preferably contains a plurality of parameters that are employed by the evoked response detection algorithm within the automatic capture detection process. For example, the set of values may contain a parameter that defines the expected amplitude of the evoked response signal for the particular patient state. Furthermore, the set of values may contain parameters that define the expected slope and width between peaks of the expected evoked response signal for the particular patient state, and other such parameters.

In an alternative embodiment, the set of values may contain a parameter that defines the expected integral of the expected evoked response signal. For example, the integral of an evoked response signal can be defined by multiplying the peak width of the signal by the amplitude of the signal. Additional parameters may also be defined in the set, including but not limited to the number of zero crossings and the peak-to-peak amplitude.

Once the set of values has been loaded, the selected parameters are used by the automatic capture detection function in the evoked response detection analysis, thereby optimizing the likelihood of correctly identifying the evoked response.

The automatic capture detection process may continue, as shown in step 220, after the operating parameters have been loaded. The process of FIG. 4 may continue to repeat while stimulation device 10 remains in operation. For example, as the automatic capture detection process continues, it may do so while using the set of values loaded in step 215. Once the automatic capture detection process identifies a different patient state, the process of refining the operating parameters may repeat.

Figure 5:
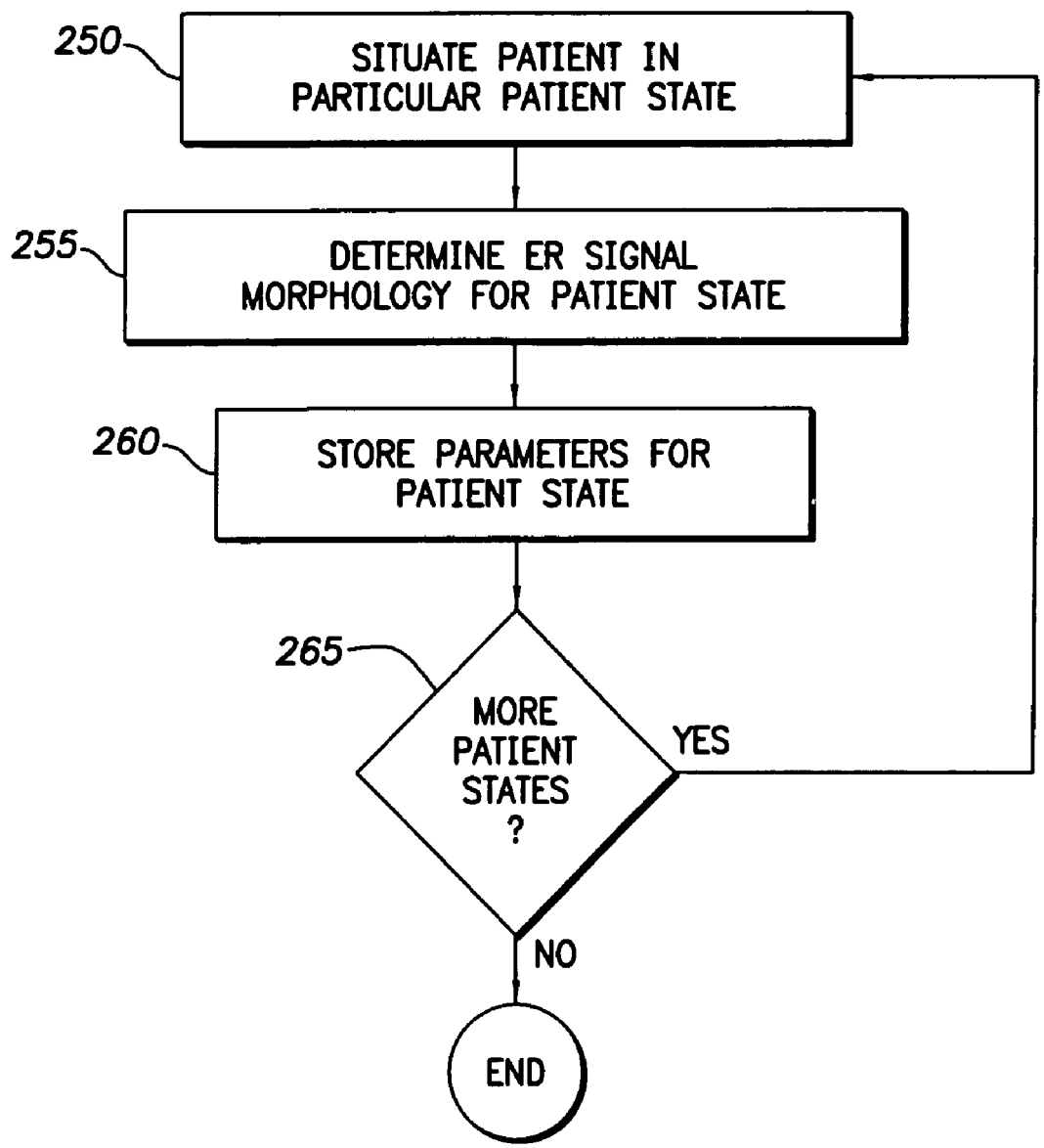
FIG. 5 is a flowchart illustrating an exemplary process for establishing parameter settings for a patient state according to one embodiment of the present invention.

FIG. 5 is a flowchart illustrating an example process for calibrating parameter settings for the respective patient states. The variable parameters that comprise a set may be initially determined at implantation of stimulation device 10. Additionally, the parameters of a set may be later modified some time after implantation of simulation device 10, according to the requirements of the physician and the needs of the patient.

A set of values may be defined or modified by physically manipulating the patient's body into the desired orientation corresponding with a patient state, as seen in step 250. For example, the patient may be placed in a standing position or an upright, sitting position. Moreover, the patient may be placed in a supine (face up) or prone (face down) position while lying down. Suitable position sensors for discriminating between these various positions are well known in the art. For example, a DC accelerometer can discriminate between supine, prone, and upright positions. Parameter settings may be established for additional positions as desired. For example, patient safety may suggest that a reclined sitting position be established if the patient is often situated in that particular orientation.

Once the patient has been properly situated, the signal morphology of the evoked response is determined, as illustrated in step 255. Certain aspects of the evoked response signal may be identified by repeated stimulation of the patient's heart in order to arrive at a normalized (or averaged) signal for the particular patient state. For example, the amplitude, width, slope, and integral of the normalized signal may be determined.

The identified parameters (i.e. those characteristics of the evoked response signal associated with the particular patient state) are stored in the memory 94 of the stimulation device 10 after those parameters have been determined, as seen in step 260. For example, the parameters that are identified may include the amplitude of the typical evoked response signal for the particular orientation, in addition to the slope of the signal, the width between peaks of the signal, the integral of the signal, and the like.

Once the parameters of the set of values have been stored in memory and have been related to the particular patient state, another patient state may be selected, as illustrated in step 265. For example, the patient may have sets of values created for the standing position, the sitting position, the supine position, the prone position, and the like. As described above, a plurality of position sets may be created as desired by the physician and beneficial for patient safety.

Figure 6:
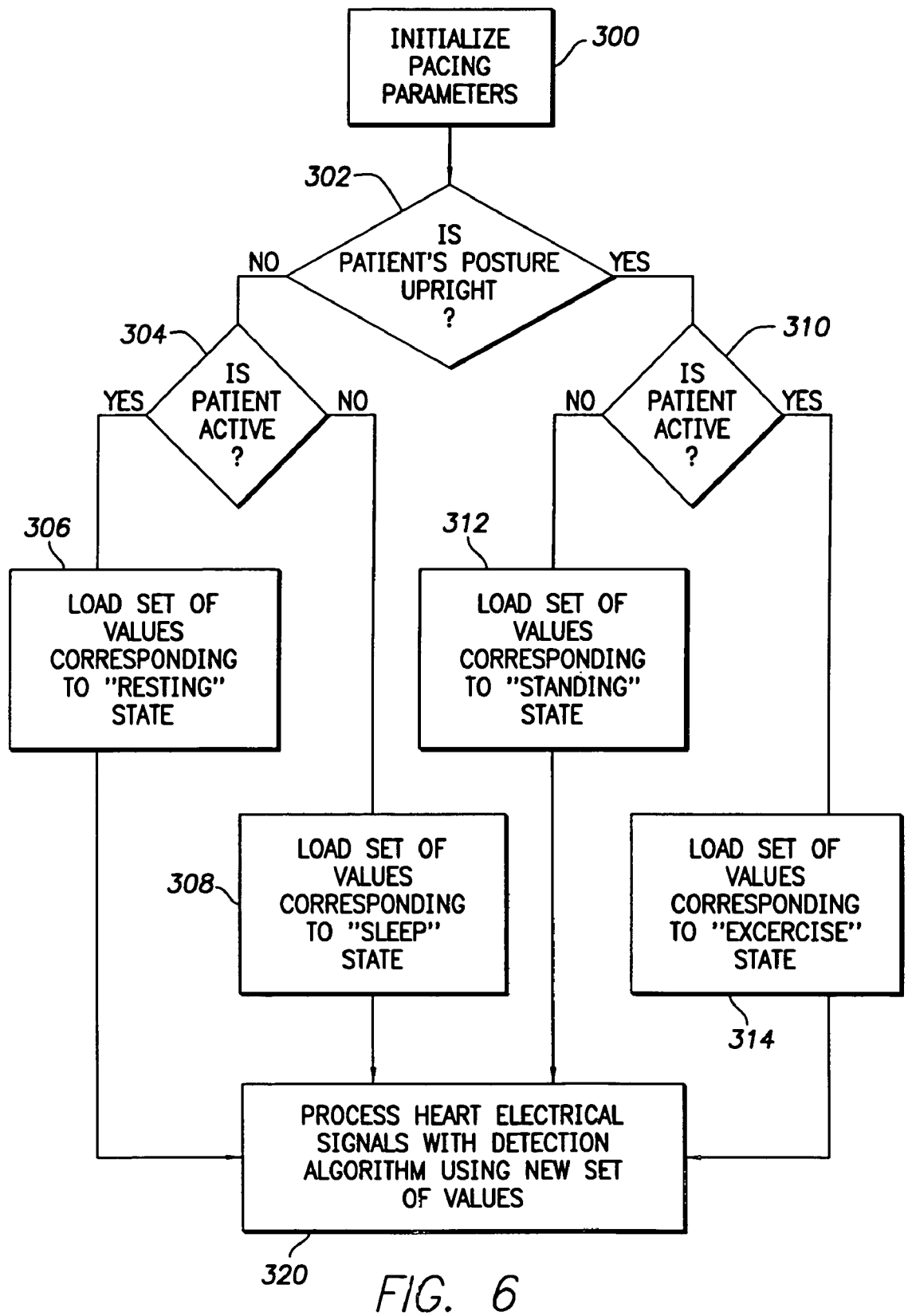
FIG. 6 is a flowchart depicting operation of one illustrative embodiment of the invention that incorporates at least two sensors to detect the patient state.

FIG. 6 is a flowchart depicting the operational flow of one illustrative embodiment of the invention. In this embodiment, the stimulation device 10 incorporates both a position sensor and an activity sensor. Operation begins at step 300, with device 10 initializing the pacing parameters to pace the patient's heart, and commencing pacing of the patient's heart. Operation then proceeds to query block 302, and the patient's posture is determined based on the signals received from the position sensor. In one embodiment, device 10 processes the signals from the position sensor to determine whether the patient is in an upright position. If not, operation proceeds to query block 304, and the patient's activity level is determined based on the signals received from the activity sensor. If at query block 304 the patient is determined to be active, then operation proceeds to step 306, the patient is determined to be in a "resting" mode, and the corresponding set of values is retrieved and loaded from memory 94. Operation then proceeds to step 320, and pacing is continued, with the detection algorithm using the loaded set of values to process the sensed responses, for example, to search for evoked responses.

If at query block 304 device 10 determines that the patient is not active, then operation instead proceeds to step 308, the patient is determined to be in "sleep" mode, and the corresponding set of values is retrieved and loaded from memory 94. Operation then proceeds to step 320.

If at query block 302 device 10 determines that the patient is in an upright position, then operation proceeds to query block 310, and device 10 determines whether the patient is currently active, by processing the signals from the activity sensor. If at query block 310 the patient is determined to not be active, then operation proceeds to step 312, the patient is determined to be standing or sitting, and the corresponding set of values is retrieved and loaded from memory 94. Operation then proceeds to step 320.

If at query block 310 the patient is determined to be active, then operation instead proceeds to step 314, the patient is determined to be exercising or otherwise active, and the corresponding set of values is retrieved and loaded from memory 320. Operation then proceeds to step 320.

It will be understood that the determination at query blocks 304 and 310 may use different thresholds to determine whether the patient is active. For example, the threshold value used for determining activity at query block 304 may be lower than the value used for determining activity at query block 310.

While in one illustrative embodiment, plural sets of parameter values are created for respective patient states, it will be understood that other types of data may be recorded for each patient state. For example, for each patient state, a template may be recorded of the evoked response morphology during calibration, with such template then being compared with a sensed response during normal operation using any well-known template matching algorithm. If a match exists (as determined by some correlation threshold), then the sensed signal is deemed an evoked response.

While preferred embodiments for detecting patient state information and incorporating same into various device parameters of cardiac stimulation devices have been shown and described, it is to be understood that these embodiments are presented by way of example only, and not limitation. As can be appreciated by those of ordinary skill in the art, the many advantages, aspects and features of the invention can be embodied in many other forms without departing from the inventive concepts contained herein. The presently disclosed embodiments, therefore, should be considered as illustrative, not restrictive. Accordingly, the invention should not be limited except by the scope of the appended claims and their equivalents.

What is claimed is:

1. A method for modifying a detection algorithm implemented by an implantable stimulation device, comprising:
   receiving one or more signals indicative of a patient state;
   processing the one or more signals to determine the patient state; and
   modifying the detection algorithm based on the determined patient state;
   wherein receiving one or more signals comprises receiving one or more position signals.

2. A method for modifying a detection algorithm implemented by an implantable stimulation device, comprising:
   receiving one or more signals indicative of a patient state;
   processing the one or more signals to determine the patient state; and
   modifying the detection algorithm based on the determined patient state;
   wherein receiving one or more signals comprises receiving one or more position signals and one or more activity signals.

3. The method of claim 2, further comprising providing plural sets of parameter values corresponding to various patient states, and wherein modifying the detection algorithm further comprises using the corresponding set of parameter values based on the determined patient state.

4. A method for detecting an evoked response in a cardiac stimulation device implanted in a patient, the device having an evoked response detection algorithm, the method comprising:
   receiving one or more signals from a position sensor;
   processing the one or more signals to determine an orientation of the patient; and
   modifying the evoked response detection algorithm based on the detected orientation of the patient.

5. The method of claim 4, wherein the evoked response detection algorithm is modified by calibrating the algorithm using one or more parameter values pertaining to the detected orientation of the patient.

6. The method of claim 4, wherein the evoked response detection algorithm is modified by selecting one or more parameter values based on the detected orientation of the patient.

7. The method of claim 5, further comprising:
   providing a first set of parameter values that correspond with a first orientation of the patient;
   providing a second set of parameter values that correspond with a second orientation of the patient; and
   modifying the set of parameter values to the first set or the second set based on the detected orientation of the patient.

8. The method of claim 4, further comprising:
   disabling an automatic capture detection function if the orientation of the patient is unstable.

9. An implantable cardiac device comprising:
   a sensor that is operative to generate one or more signals indicative of a patient state; and
   a controller that is in communication with the sensor, the controller being programmed to apply a detection algorithm to received electrical activity signals, wherein the controller is operative to receive the one or more signals from the sensor, process the one or more signals to determine the patient state, and adjust one or more parameter values of the detection algorithm based on the determined patient state;
   wherein the sensor comprises a position sensor.

10. An implantable cardiac device comprising:
    a sensor that is operative to generate one or more signals indicative of a patient state; and
    a controller that is in communication with the sensor, the controller being programmed to apply a detection algorithm to received electrical activity signals, wherein the controller is operative to receive the one or more signals from the sensor, process the one or more signals to determine the patient state, and adjust one or more parameter values of the detection algorithm based on the determined patient state;

wherein the sensor comprises a position sensor, and further comprising an activity sensor that is operative to generate one or more signals Indicative of an activity level of the patient.

11. The implantable cardiac device of claim 10, wherein the controller is operative to maintain a plurality of sets of parameter values corresponding to the respective patient states, and wherein the controller adjusts the detection algorithm by using one of the sets of parameter values based on the detected patient state.

12. An implantable cardiac device comprising:

a memory configured to store plural sets of parameter values corresponding to various patient states;

a sensor that is operative to generate one or more signals indicative of a patient state; and a controller that is operative to receive the one or more signals from the sensor, process the one or more signals to determine the patient state, and use the corresponding set of parameter values to process sensed electrical activity;

wherein the controller is configured to modify an evoked response detection algorithm by:

retrieving a position set comprising a plurality of parameter values pertaining to the orientation of the patient; and calibrating the evoked response detection algorithm using the position set of parameter values,.

13. The system of claim 12, wherein the controller is configured to calibrate the evoked response detection algorithm by:

replacing the position set of parameter values with a new position set of parameter values in the evoked response detection algorithm; and employing the new operating set in the evoked response detection algorithm.

14. The system of claim 12, wherein the controller is further configured to:

establish a first setting for the position set of parameter values when the patient is vertically oriented;

establish a second setting for the position set of parameter values when the patient is horizontally oriented; and modify the set of parameter values to the first setting or the second setting based on the orientation of the patient.

15. An implantable cardiac device comprising:

a memory configured to store plural sets of parameter values corresponding to various patient states;

a sensor that is operative to generate one or more signals indicative of a patient state; and a controller that is operative to receive the one or more signals from the sensor, process the one or more signals to determine the patient state, and use the corresponding set of parameter values to process sensed electrical activity;

wherein the controller is further configured to disable an automatic capture detection function to prevent false loss of capture detection when the signal indicates that an orientation of the patient is changing.

16. An implantable cardiac device comprising:

a computer readable medium encoded with an evoked response detection algorithm;

a position sensor to generate one or more position signals indicative of an orientation of a patient; and a controller to receive the one or more position signals from the position sensor, to process the one or more position signals to determine the orientation of the patient, and to modify the evoked response detection algorithm computer based on the detected orientation of the patient.

17. The implantable cardiac device of claim 16, wherein the evoked response detection algorithm is modified by calibrating the algorithm using one or more parameter values pertaining to the detected orientation of the patient.

18. The implantable cardiac device of claim 16, wherein the evoked response detection algorithm is modified by selecting one or more parameter values based on the detected orientation of the patient.

19. The implantable cardiac device of claim 17, further comprising:

a first set of parameter values that correspond with a first orientation of the patient; and a second set of parameter values that correspond with a second orientation of the patient; and wherein the set of parameter values is modified to the first set or the second set based on the detected orientation of the patient.

* * * * *